US008618323B2

(12) United States Patent
Benz et al.

(10) Patent No.: US 8,618,323 B2
(45) Date of Patent: Dec. 31, 2013

(54) LIGHT FILTERS COMPRISING A NATURALLY OCCURRING CHROMOPHORE AND DERIVATIVES THEREOF

(75) Inventors: Patrick H. Benz, Sarasota, FL (US); Jose A. Ors, Sarasota, FL (US)

(73) Assignee: Benz Research and Development Corporation, Sarasota, FL (US)

( * ) Notice: Subject to any disclaimer, the term of this patent is extended or adjusted under 35 U.S.C. 154(b) by 0 days.

(21) Appl. No.: 13/016,829

(22) Filed: Jan. 28, 2011

(65) Prior Publication Data

US 2011/0166381 A1 Jul. 7, 2011

Related U.S. Application Data

(63) Continuation-in-part of application No. 12/042,317, filed on Mar. 4, 2008, now Pat. No. 8,026,326.

(60) Provisional application No. 60/893,065, filed on Mar. 5, 2007.

(51) Int. Cl.
C07C 217/84 (2006.01)
C07C 223/06 (2006.01)
C07C 225/22 (2006.01)

(52) U.S. Cl.
USPC ........... 560/221; 560/142; 560/250; 560/254; 564/305; 564/443; 568/306; 568/335; 568/424; 568/584; 568/442

(58) Field of Classification Search
USPC .......... 560/142, 221, 250, 254; 564/305, 443; 568/306, 335, 424, 584, 442
See application file for complete search history.

(56) References Cited

U.S. PATENT DOCUMENTS

| 4,555,570 | A  | 11/1985 | Kanojia et al. |
|-----------|----|---------|----------------|
| 5,532,289 | A  | 7/1996  | Benz et al.    |
| 5,891,932 | A  | 4/1999  | Benz et al.    |
| 6,011,081 | A  | 1/2000  | Benz et al.    |
| 6,096,799 | A  | 8/2000  | Benz et al.    |
| 6,242,508 | B1 | 6/2001  | Benz et al.    |
| 6,245,830 | B1 | 6/2001  | Benz et al.    |
| 6,265,465 | B1 | 7/2001  | Benz et al.    |
| 6,267,784 | B1 | 7/2001  | Benz et al.    |
| 6,517,750 | B2 | 2/2003  | Benz et al.    |
| 6,555,598 | B2 | 4/2003  | Benz et al.    |
| 6,566,417 | B2 | 5/2003  | Benz et al.    |
| 6,599,959 | B2 | 7/2003  | Benz et al.    |
| 6,627,674 | B2 | 9/2003  | Benz et al.    |
| 6,825,975 | B2 | 11/2004 | Gallas         |
| 7,067,602 | B2 | 6/2006  | Benz et al.    |
| 2005/0041299 | A1 | 2/2005 | Gallas       |
| 2006/0293350 | A1 | 12/2006 | Alanine et al. |

FOREIGN PATENT DOCUMENTS

| GB | 868 880 A       | 5/1961  |
|----|-----------------|---------|
| JP | 06-157579       | 6/1994  |
| JP | 06 157579 A     | 6/1994  |
| JP | 10-228113       | 8/1998  |
| JP | 2005-272413     | 10/2005 |
| JP | 2007-503023     | 2/2007  |
| JP | 2007-106745     | 4/2007  |
| WO | WO-2005/014677  | 2/2005  |
| WO | WO-2005/019874  | 3/2005  |
| WO | WO 2006/074843 A | 7/2006 |

OTHER PUBLICATIONS

STN structure summary (document No. 116:41149, dated Feb. 8, 1992) of Gould et al. (Tetrahedron 47 (1991)7209.*
STN structure summary (document No. 119:72411, dated Aug. 21, 1993) of Fukuyama et al. (Tetrahedron Letters 34 (1993) 2577.*
PCT/US2008/055834 filed Mar. 4,2008, Intl. Search Report, Dec. 4, 2008 (2 pages).
Allcock et al., *Contemporary Polymer Chemistry*, Prentice Hall (1982)., Table of Contents.
Benz et al., 46 *Global Contact* 55 (2007).
Billmeyer, *Textbook of Polymer Science*, Wiley-Interscience (3rd ed.1984)., Table of Contents.
Bova et al., 42 *Investigative Ophthalmology and Visual Science* 200-205 (2001).
Gaillard et al, 41 *Investigative Ophthalmology and Visual Science* 1454 (2000).
Smith, M. et al., *March's Advanced Organic Chemistry, Reactions, Mechanism, and Structure* (5th edition 2001)., Table of Contents.
Notice of Reasons for Rejection, Japanese Patent Application No. 2009-552844, Dispatch Date Oct. 22, 2012, 6 pages. (w/English Translation).

* cited by examiner

*Primary Examiner* — Roberto Rabago
(74) *Attorney, Agent, or Firm* — Foley & Lardner LLP (57) ABSTRACT

A composition comprising a polymer backbone and at least one side group, wherein the side group comprises a benzene ring-based chromophore comprising a ketone at the 1-position, a substituted or unsubstituted amino group at the 2-position, and an oxygen atom at the 3-position of the benzene ring. The chromophore is a kynurenine-based compound. Methods of making and using the composition are also provided. The composition can be used in an ophthalmic lens or device for protecting the retina by blocking UV rays and filtering violet rays.

21 Claims, 7 Drawing Sheets

LIGHT FILTERS COMPRISING A NATURALLY OCCURRING CHROMOPHORE AND DERIVATIVES THEREOF

PRIORITY

This application is a Divisional of U.S. application Ser. No. 12/042,317, filed Mar. 4, 2008 now U.S. Pat. No. 8,026,326, and also claims priority to U.S. Application Ser. No. 60/893,065, filed Mar. 5, 2007, which are each incorporated by reference in their entirety for all purposes.

BACKGROUND

There have been a variety of proposed dyes for use as polymerizable compounds to affect the colorization of optical plastics for lenses and ocular devices. Most of these relate to various diphenyl azo or triphenyl diazo compounds. These generally claim to provide UV protection as well as blue light blocking capability because of their yellow or orange-yellow color. Because the human crystalline lens is pale yellow in color in young people and a brownish yellow color in older people, these dyes serve the purpose of providing UV protection in addition to blue light filtering capability.

In addition, U.S. Pat. No. 6,825,975 (Gallas) discloses a light filter prepared by oxidatively polymerizing 3-hydroxykynurenine to form complex visible light absorbing compounds that have a very broad absorption spectrum that is very different from 3-hydroxykynurenine. Moreover, this system is limited to oxidatively polymerized 3-hydroxykynurenine and does not provide versatility and tunability. Moreover, this system only provides blue light filtering capability. The amino acid functionality is still present.

A need exists to provide, for example, more discrete structures which are easier to make and provide better and more versatile performance which can be tuned to particular applications.

SUMMARY

Provided herein are embodiments comprising compounds, compositions, polymers, articles, methods of making, and methods of using. Chromophores are derived herein from naturally occurring kynurenine and derivatives thereof.

For example, one embodiment ("Embodiment 1") comprises a composition comprising: a compound comprising a polymerizable vinyl group covalently linked to a benzene ring-based chromophore comprising a ketone at the 1-position, a substituted or unsubstituted amino group at the 2-position, and an oxygen atom at the 3-position of the benzene ring, wherein the chromophore does not comprise an oxidative polymerization product of 3-hydroxykynurenine.

Another embodiment provides a composition comprising: a compound comprising a polymerizable vinyl group covalently linked to a benzene ring comprising a chromophore comprising a ketone at the 1-position, a substituted or unsubstituted amino group at the 2-position, and an oxygen atom at the 3-position of the benzene ring, wherein the chromophore does not comprise an oxidative polymerization product of 3-hydroxykynurenine.

Another embodiment ("Embodiment 21") provides a composition comprising: a compound comprising a polymerizable vinyl group covalently linked to a benzene ring-based chromophore comprising a ketone at the 1-position, a substituted or unsubstituted amino group at the 2-position, and an oxygen atom at the 3-position of the benzene ring, wherein the chromophore comprises a substituent at the ketone of the 1-position of the benzene ring which does not comprise an amino acid group.

Another embodiment provides a composition comprising: a compound comprising a polymerizable vinyl group covalently linked to a benzene ring comprising a chromophore comprising a ketone at the 1-position, a substituted or unsubstituted amino group at the 2-position, and an oxygen atom at the 3-position of the benzene ring, wherein the chromophore comprises a substituent at the ketone of the 1-position of the benzene ring which does not comprise an amino acid group.

Another embodiment provides a composition comprising: A composition comprising: a polymer comprising a polymer backbone and at least one side group, wherein the side group comprises a benzene ring-based chromophore comprising a ketone at the 1-position, a substituted or unsubstituted amino group at the 2-position, and an oxygen atom at the 3-position of the benzene ring.

Another embodiment provides a composition comprising: a polymer comprising a polymer backbone and at least one side group, wherein the side group comprises a benzene ring comprising a chromophore comprising a ketone at the 1-position, a substituted or unsubstituted amino group at the 2-position, and an oxygen atom at the 3-position of the benzene ring.

Another embodiment provides a composition comprising: a polymer consisting essentially of a polymer backbone and at least one side group, wherein the side group comprises a benzene ring comprising a chromophore comprising a ketone at the 1-position, a substituted or unsubstituted amino group at the 2-position, and an oxygen atom at the 3-position of the benzene ring.

Another embodiment provides a method of making comprising: providing a polymerization monomer according to embodiment 1 or 21, optionally providing at least one additional polymerization monomer, polymerizing the polymerization monomers.

Another embodiment includes a compound represented by wherein $R_1$ is H, an alkyl group, or comprises an amino acid moiety or derivative thereof; wherein $R_2$ and $R_3$ are individually H, alkyl, or any moiety with a vinyl functionality; wherein $R_4$ is an alkyl group, any moiety with a vinyl functionality, a counterpart alkylene group, or a sugar moiety; and wherein X is an optional electron-donating group linked to the benzene ring at the 4, 5, or 6 position.

Another embodiment includes a compound represented by wherein R is H, an alkyl group, or comprises an amino acid moiety or derivative thereof; wherein L is a linker; and wherein PVG is a polymerizable vinyl group.

Another embodiment includes a compound represented by

In another embodiment, monomers of the compounds, compositions, polymers, articles and methods include a linker.

In another embodiment, the polymers comprise a carbon backbone.

Advantages include a synthetically diverse system which can be tuned to particular applications and compounds which bear moieties which use the advantages of the natural eye system. For example, fine shades of color and fluorescent properties can be tuned which are not provided with conventional UV-blockers.

Additional advantages include blocking UV-A and filtering violet light to a greater degree than 3-hydroxykynurenine in saline.

Suitable applications include an ophthalmic lens or device. The device can be a hard lens, contact lens, intraocular lens, eyeglass, sunglass or other protective eyewear for protecting the retina from UV and violet rays. Other applications include a window, screen and any other non-ophthalmic device for protecting the retina from UV and violet rays. The devices are adaptable for human use.

In one embodiment, the compounds or compositions, upon polymerization, are suitable for use in ophthalmic lenses or devices.

DETAILED DESCRIPTION

Introduction

All references cited herein are incorporated by reference herein in their entirety.

Compounds described herein include both D- and L-forms, and mixtures thereof, unless otherwise specified.

Lens materials including polymeric hydrophilic and hydrophobic lens materials are known in the art. For example, U.S. Pat. Nos. 5,532,289; 5,891,932; 6,011,081; 6,096,799; 6,242,508; 6,245,830; 6,265,465; 6,555,598; 6,566,417; 6,599,959; and 6,627,674 describe contact lens material, monomers, crosslinkers, hydrogels, and methods of making the same, and are incorporated herein by reference. Improved properties of said lenses include improved mechanical strength, water retention and dimensional stability. Additional information and products can be obtained from Benz R&D (Sarasota, Fla.).

U.S. Pat. Nos. 6,267,784, 6,517,750 and 7,067,602 describe intraocular lens (IOL) materials and methods of making the same, and are incorporated herein by reference. The IOL may be a one piece unit with an optic portion and a haptic portion. The IOL materials can be formed with methacrylate monomers such as alkoxy-alkylmethacrylate. Some of the improved properties include good water retention and dimensional stability. Also described are IOL materials additionally enhanced with crosslinking agents and UV absorbents.

Polymers, crosslinked polymers, copolymers, terpolymers, hydrogels, interpenetrating polymer networks, random versus block microstructures, oligomers, monomers, methods of polymerization and copolymerization, molecular weight, measurements, and related materials and technologies are generally known in the polymer arts and can be used in the practice of the presently described embodiments. See, for example, (1) *Contemporary Polymer Chemistry*, Allcock and Lamp, Prentice Hall, 1981, and (2) *Textbook of Polymer Science*, $3^{rd}$ Ed., Billmeyer, Wiley-Interscience, 1984. Free radical polymerization can be used to prepare the polymers herein.

Hydration of crosslinked polymers is known in the art in various technologies including hydrogel, membrane, and lens materials.

Polymers used for optical applications, including IOL and contact lens, can be hydrophilic or hydrophobic. Hydrophobic polymers do not substantially hydrate and do not become hydrogels.

Suitable monomers for the polymers include polymerizable vinyl groups. However, other polymerizable groups known in the art to create either hydrophilic or hydrophobic polymers are also suitable.

The term (meth)acrylate refers to both methacrylate or acrylate embodiments as understood by one skilled in the art. Methacrylate embodiments are preferred over acrylate embodiments.

Synthetic methods of organic chemistry are known in the art including for example J. March, *Advanced Organic Chemistry, Reactions, Mechanism, and Structure*, $5^{th}$ edition, as well as previous editions.

Presently claimed embodiments relate to polymerizable chromophore or dye comprising a particular type of chromophore with the same or nearly or substantially the same UV and visible light absorption characteristics as the natural UV filters or a primary natural UV filter of the human crystalline lens. In one embodiment, these compounds, chromophores or dyes can be polymerized into a polymer matrix of the materials that are used as ocular devices and lenses such as for example eye glasses, sun glasses, contact lenses, and intraocular lenses.

As used herein, alkyl groups can be for example linear, branched, or cyclic alkyl groups. They can be for example $C_1$ to $C_{30}$ alkyl groups.

As used herein, aryl groups can comprise one or more aromatic rings and can comprise substituents on the rings.

Compound and Benzene- and/or Kynurenine-Based Chromophore

Kynurenine compounds and derivatives thereof are known in the art. For example, Bova et al., *Investigative Ophthalmology and Visual Science,* 2001, 42, 200-205 describe age-dependent human lens coloration based on the natural UV filters contained in the human lens including for example 3-hydroxykynurenine, kynurenine, 3-hydroxykynurenine glucoside, and glutathionyl-3-hydroxykynurenine glucoside. Also, Gaillard et al, *Investigative Ophthalmology and Visual Science,* 2001, 41, 1454-1459 also describes kynurenine investigations related to the yellowing of lens protein with age. See also U.S. Pat. No. 6,825,975.

The kynurenine structure in nature, including derivatives thereof, can provide therefore a benzene ring-based chromophore having a benzene ring, a ketone group at the 1-position of the benzene ring, a substituted or unsubstituted amino group at the 2-position of the benzene ring, and an oxygen atom at the 3-position of the benzene ring. It can comprise the 2-amino-3-hydroxybenzoyl based structure which can be derivatized and in particular derivatives to comprise a moiety which allows covalent attachment to a larger polymer matrix. Benz et al., *Global Contact,* 2007, 46, 55-58, describe a kynurenine-based compound in an intraocular lens.

Figure 1:
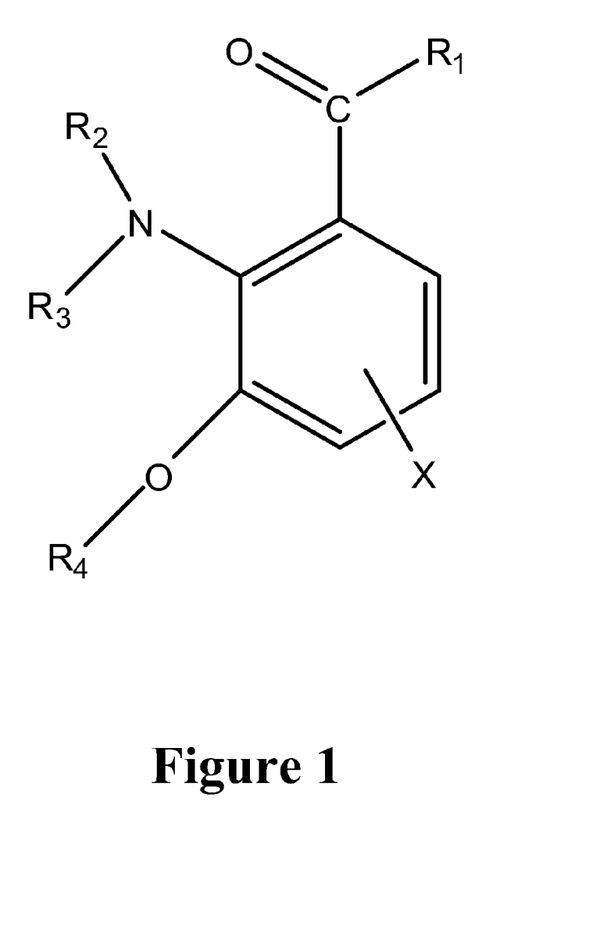
FIG. 1 illustrates a generic chemical formula for a chromophore.

The compound comprising the Kynurenine-based chromophore can be represented by the formula in FIG. 1, for example which also shows the numbering system for the base aromatic benzene ring of the kynurenine-derived or -based chromophore. For example, the carbonyl group is bonded at $C_1$, the amino group is bonded at $C_2$, and the oxygen atom is bonded at $C_3$, and the optional X group can attach at $C_4$, $C_5$, or $C_6$.

The $R_1$ group can be, for example, linked to the carbonyl of the aromatic group 1-position via an O, N, or C. $R_1$ can be H. However, the $R_1$ group can be adapted so that the absorption properties based on the aromatic ring of kynurenine are not substantially changed by the $R_1$ group. $R_1$ can be for example an alkyl group such as methyl or ethyl or propyl. $R_1$ can be a group comprising an amino acid moiety or derivative thereof. However, one embodiment provides that $R_1$ is free of amino acid group and derivatives thereof. Alkyl groups include $C_1$ to $C_{20}$ groups.

The $R_2$ group and the $R_3$ group can be the same or different independently of each other. $R_2$, $R_3$, or both can be H. For example, $R_2$ and $R_3$ can be for example an alkyl group such as methyl, ethyl, propyl, isopropyl, butyl, isobutyl, tertbutyl, metacroyl, acryoyl, or any moiety with a vinyl functionality. Alkyl groups include $C_1$ to $C_{20}$ groups.

The $R_4$ group can be for example an alkyl group such as methyl, ethyl, propyl, isopropyl, butyl, isobutyl, tertbutyl, metacroyl, acryoyl, or any moiety with a vinyl functionality, or counterpart alkylene groups such as methylene, ethylene, propylene, butylene, and the like. Alkyl and alkylene groups include $C_1$ to $C_{20}$ groups.

R4 can comprise for example a sugar moiety such as a glucose moiety. In one embodiment, the oxygen atom at the 3-position of the kynurenine-based chromophore is bonded to an aliphatic carbon atom or a saturated carbon atom.

The X group is optional and can be linked to the benzene ring at the 4, 5, or 6 position. The X group can be an electron-donating substituent or group which can be used to tune the desired absorption for a particular application. Increased donation to the ring can shift absorbance to longer wavelength. In other words, the kynurenine-based chromophore can comprise at least one electron donating substituent in the 4-, 5-, or 6-position of the kynurenine benzene ring. For example, the electron donating group can be an alkyl group, an —OR group such as alkoxy, or a substituted amino group. Electronic donating groups are described in for example J. March, *Advanced Organic Chemistry, Reactions, Mechanism, and Structure,* $5^{th}$ edition, as well as previous editions.

In one embodiment, the amino group at the 2-position is an —$NH_2$ group, an —$NHR_2$ group, or an —$NR_2R_3$ group (wherein $R_2$ and $R_3$ can be H).

In one embodiment, the carbonyl group at the 1-position is derivatized with an alkyl group.

In one embodiment, the compound is represented by Formula I.

In one embodiment, the compound is represented by Formula II.

In one embodiment, the compound is represented by Formula III.

In one embodiment, the compound is suitable for use in ophthalmic lenses or devices. For example, the polymerizable compound can be formulated to be compatible and soluble with other monomers and mixtures so that good polymerization and homogeneity can be achieved.

Figure 2:
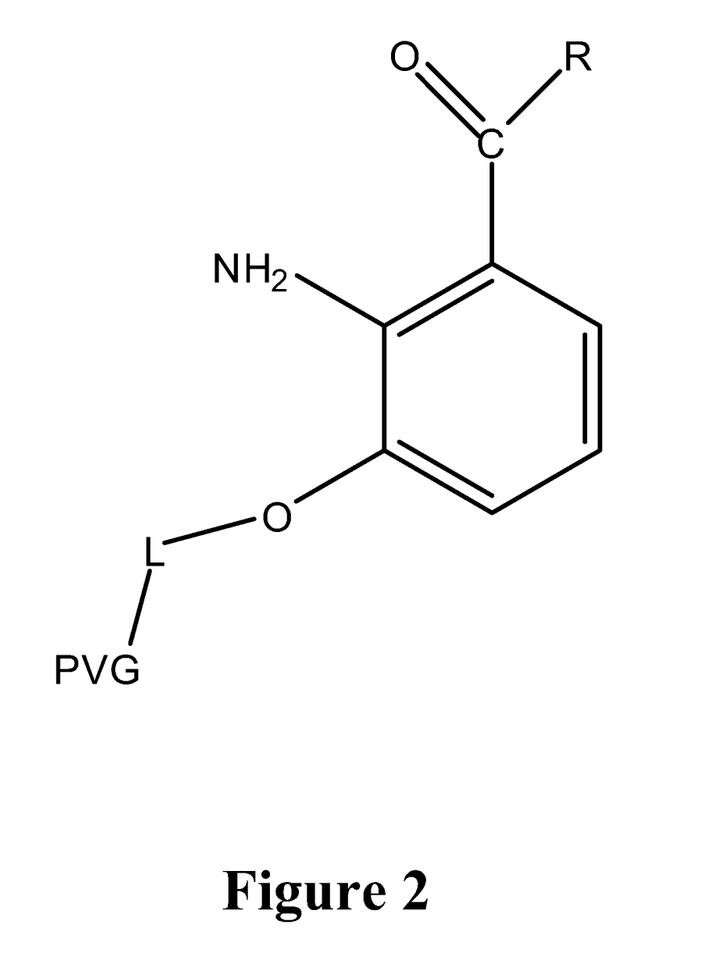
FIG. 2 illustrates a generic chemical formula for a chromophore (PVG is polymerizable vinyl group, L is linker).
Figure 3:
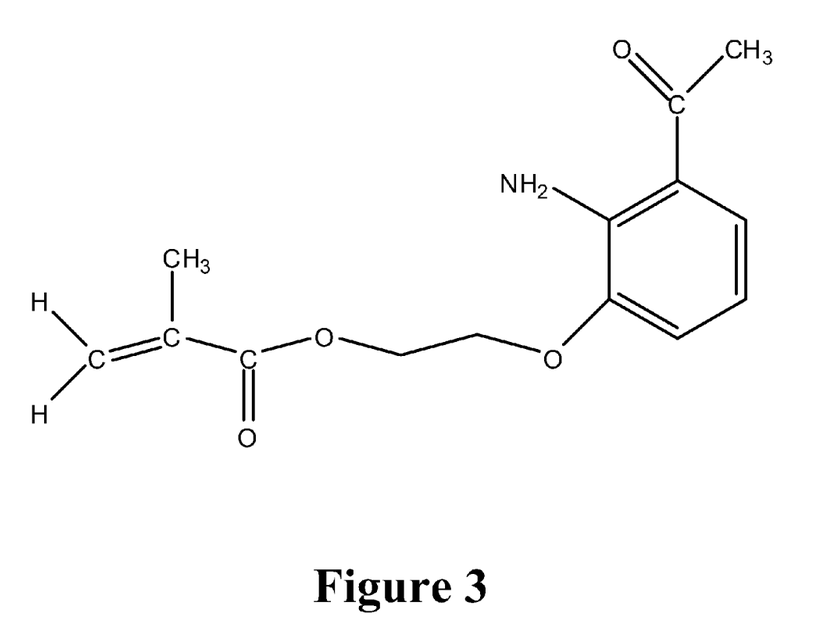
FIG. 3 illustrates a particular embodiment.

Compounds represented by the formulas in FIGS. 1, 2, and 3, respectively, can have a variety of molecular weights including for example 1,000 g/mol or less, 500 g/mol or less, or 250 g/mol or less.

Polymerizable Vinyl Group

The polymerizable vinyl group can be linked to the benzene ring-based chromophore via a linker group.

For example, the polymerizable vinyl group can be linked to the benzene ring-based chromophore at the 3-position of the benzene ring.

Alternatively, the polymerizable vinyl group can be linked to the benzene ring-based chromophore at the 2-position of the benzene ring.

Alternatively, the polymerizable vinyl group can be linked to the benzene ring-based chromophore at the 4-, 5-, or 6-position of the benzene ring.

Alternatively, the polymerizable vinyl group can be linked to the benzene ring-based chromophore at the 1-position of the benzene ring.

The linker group can for example provide flexibility to the molecule and separate the chromophore from the polymer backbone. The linker group can be also referred to as a spacer group. The linker group can be for example an alkylene group free of heteroatoms. The linker moiety can be for example a $C_1$ to $C_{20}$ group, or a $C_1$ to $C_{10}$ group, or a $C_2$ to $C_5$ group. Alternatively, the linker moiety can comprise one or more heteroatoms such as oxygen as found in for example ethylenoxy or propyleneoxygroups. In one embodiment, for example, the polymerizable vinyl group is linked to the benzene ring-based chromophore via an alkylene or alkyleneoxy linker group.

In particular, the linker or spacer group can be a linear chain of atoms connecting a vinyl polymer backbone including a (meth)acrylate polymer backbone and the chromophore and comprising for example one, two, three, four, five, or six atoms in the chain. Methylene units (—$CH_2$—) and oxygen atoms can be used. One skilled in the art can adjust the length of the spacer to adapt to the particular need and the other components of the formulation. If the spacer group becomes too large, in some embodiments the mechanical properties of the parent polymer become undesirable. The atoms can be for example carbon atoms or can be a heteroatom such as oxygen. The linear chain can comprise substituents such as hydrogen. Examples of spacers include —CH₂— and —CH₂CH₂— and —CH₂CH₂OCH₂CH₂— and —OCH₂CH₂OCH₂CH₂—.

The polymerizable vinyl group can be polymerized by free radical polymerization by methods known in the art including use of initiators. In one embodiment, the polymerizable vinyl group comprises a methacrylate or acrylate moiety.

Covalent Linkage

The polymerizable vinyl group can be directly or indirectly covalently linked to the chromophore including through use of a linker group.

Does not Comprise Oxidatively-Polymerized 3-Hydroxykynurenine

The compound comprising the kynurenine-derived and benzene-ring based chromophore can be adapted so that it does not encompass compounds described in U.S. Pat. No. 6,825,975 (Gallas) based on oxidative polymerization product of 3-hydroxykynurenine. A basic and novel feature of this embodiment is that the composition and compounds are free or substantially free of oxidative polymerization product of 3-hydroxykynurenine.

In one embodiment, the kynurenine-derived chromophore does not polymerize to form a polyphenol.

Polymers and Polymerization

The crosslinked polymer, as known in the art, can comprise various different monomeric subunits which can be represented by, for example:

$$\text{-[A]}_a\text{-[B]}_b\text{-[C]}_c\text{-[D]}_d\text{-} \quad \text{(I)}$$

wherein for example A represents a hydrophilic monomeric subunit; B represents an alkoxyalkyl monomeric subunit, C represents a monomeric subunit comprising a kynurenine-based chromophore, and D represents a crosslinker monomeric subunit, and wherein the monomeric subunits are or are not randomly dispersed along the monomer chain. In another embodiment, both A and B can be adapted to provide a hydrophobic polymer. In some cases, some block character can be present in the distribution of monomeric subunits. The polymer chain can be a linear polymer chain apart from the crosslinker subunits which provide covalent or other types of linkage sites between the chains.

The end groups of the copolymer are not particularly limited but can be for example determined by the initiator used and the termination mechanisms present in the copolymerization reaction.

One embodiment is for a polymer which consists essentially of polymer subunits which substantially exclude those ingredients and subunits which compromise the basic and novel properties of the materials.

In one embodiment, the polymer is not a polyphenol.

Polymerization conditions including initiator or catalyst selection can be selected to provide for clean polymerization so that for example there is little if any hydrogen abstraction or chain-transfer.

The hydrophobic and hydrophilic character of the polymer backbone, linker or spacer groups, side groups, and chromophore can be tailored for good compatibility and the desired solubility and swellability. The polymer can be hydrophobic, resulting in a rubber or glassy polymer, depending on its glass transition temperature ($T_g$).

Monomeric subunits comprising hydrophilic moieties to provide hydrophilic properties are known in the art, see for example U.S. Pat. No. 6,517,750, which is hereby incorporated by reference in its entirety. For example, polar groups can be present comprising for example oxygen or nitrogen atoms, and groups capable of hydrogen bonding. This component facilitates water absorption. The amount of this component, along with amounts of more hydrophobic components, can be adjusted to provide a desired water uptake.

One embodiment makes use of HO—R-MA, wherein R is a spacer group between the HO— hydroxyl and the methacrylate, and R is an alkyl group of 1 to 6 carbon atoms.

A possible material is 2-HEMA and in particular, highly pure forms of 2-HEMA, e.g., 99.9% pure, as the material may be in the eye for long periods of time. Content of ions and acid should be as close to zero as possible. For example, acidic impurities such as methacrylic acid can result in particle formation over time such as for example calcium phosphate particle formation.

Monomeric subunits which comprise alkoxyalkyl groups are known in the art, see for example U.S. Pat. No. 7,067,602 and U.S. Pat. No. 6,517,750, which are hereby incorporated by reference in its entirety.

One embodiment makes use of $R_5$—O—$R_6$-MA, wherein $R_5$ and $R_6$ can be independently an alkylene or alkyl group with 1 to 6 carbon atoms, and MA is methacrylate. The presence of this subunit provides advantageous mechanical properties to the polymer.

The amount of this subunit can be adjusted to control the amount of water uptake. The polymer can be hydrophobic, allowing minimal uptake of water.

Crosslinker subunits, including acrylates and methacrylates, are well-known in the art. They can be the result of crosslinking of difunctional or trifunctional or even tetrafunctional monomers such as a di(meth)acrylate or a tri(meth) acrylate. The crosslink density can also be controlled to control the amount of water present as well as the mechanical properties.

Monomers which can provide crosslinker subunits can be represented by R(X1)$_n$, wherein R is a core organic group such as a $C_2$, or $C_3$ or $C_4$ or $C_5$ or $C_6$ group, with or without heteroatoms like oxygen, $X_1$ is a reactive group such as acrylate or methacrylate, and n is the number of reactive groups such as 2, 3, or 4.

They can be prepared from a variety of multifunctional olefinic monomers such as, for example, ethyleneglycol dimethacrylate (EGDMA), trimethylol propane trimethacrylate (TMPTMA), trimethylol propane triacrylate (TMPTA), diethyleneglycoldimethacrylate (DiEGDMA), triethyleneglycoltrimethyacrylate (TriEGDMA), and the like. A preferred example is trimethylol propane trimethacrylate. The amounts of the various subunits can be adapted to provide the requisite balance of optical properties and mechanical properties, including hydrophobicity, clarity, folding ability, refractive index, and the like.

The amounts of the monomers can be adapted for a particular application and are not particularly limited to the extent the desired physical properties can be achieved. For example, the amount of hydrophilic (meth)acrylate subunits can be for example about 50 wt. % to about 80 wt. %, or about 55 wt. % to about 75 wt. %, or about 60 wt. % to about 70 wt %.

The amount of the alkoxyalkyl(meth)acrylate subunits can be for example about 10 wt. % to about 35 wt. %, or about 15 wt. % to about 30 wt. %.

The amount of the subunits comprising chromophore can be for example about 5 wt. % to about 25 wt. %, or about 10 wt. % to about 20 wt. %.

The amount of the crosslinker can be for example about 0.01 wt. % to about 2.5 wt. %, or about 0.1 wt. % to about 1.5 wt. %, or about 0.2 wt. % to about 1 wt. %.

The amounts of the initiator, before polymerization, is not particularly limited but can be for example 0.02 wt. % to about 0.40 wt. %, or about 0.02 wt. % to about 0.15 wt. %, or about 0.05 wt. % to about 0.20 wt. %, or about 0.05 wt. % to about 0.10 wt. %.

The amounts of the subunits can in many cases be approximated by the amounts of the monomers used to make the polymer.

In one embodiment, the polymer is a polymerized form of the compound represented by Formula I. In addition, the polymer can be crosslinked and modified with comonomers.

In one embodiment, the polymer is a polymerized form of the compound represented by Formula II. The polymer can be crosslinked and modified with comonomers.

In one embodiment, the polymer is a polymerized form of the compound represented by Formula III. The polymer can be crosslinked and modified with comonomers.

Methods of Making

Compounds can be made and polymerizations conducted by methods known in the art of synthetic organic chemistry and polymer chemistry.

For example, 2-Amino-3-ethoxymethacroyl acetophenone (shown in FIG. 3) can be prepared as follows:

2-Amino-3-hydroxyacetophenone (AHA) is obtained. Chloroethanol is added to AHA under basic conditions giving the hydroxyethylether at the 3-position. After workup, methacroyl chloride is added to the hydroxyethylether giving 2-Amino-3-ethoxymethacroyl acetaphenone. AHA is commercially available from, for example, TCI America (Tokyo Chemica Industries).

This is a two step process but in principle a one step process can be also used wherein an R—Cl group is condensed with an —OH group to link together the polymerizable vinyl compound and the chromophore. Materials may be harder to find in a one step process.

Application

Suitable applications include an ophthalmic lens or device. The device can be a hard lens, contact lens, intraocular lens, eyeglass, sunglass or other protective eyewear for protecting the retina from UV and violet rays. Other applications include a window, screen and any other non-ophthalmic device for protecting the retina from UV and violet rays.

WORKING EXAMPLES

Additional description is provided by the following non-limiting working examples.

Spectral Properties

Figure 4:
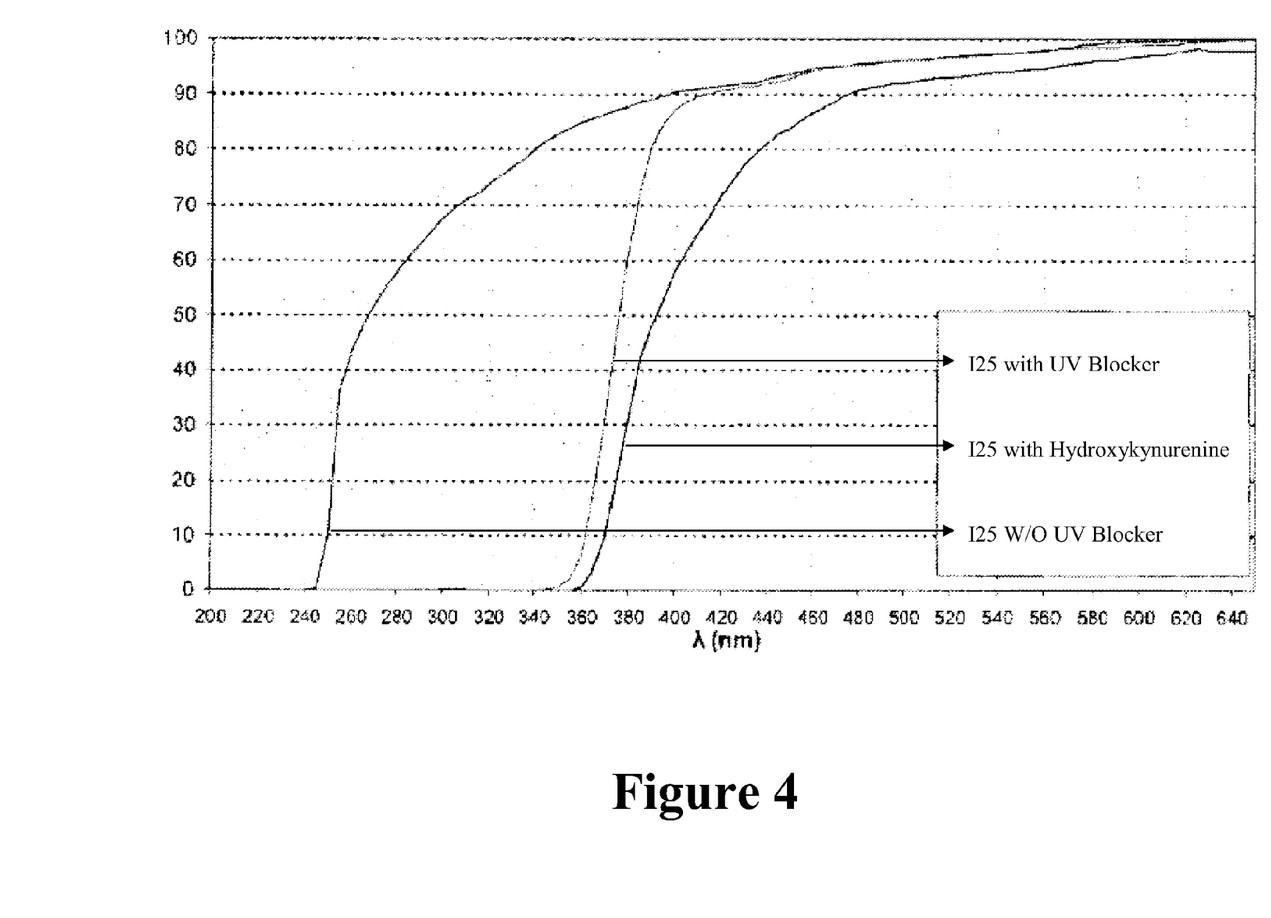
FIG. 4 illustrates transmission spectral properties.

FIG. 4 illustrates the blue-blocking, UV-blocking and violet-blue filtering effect of 3-hydroxykynurenine. Three transmission spectra are shown of a hydrophilic intraocular lens material including IOL 25 material of (ethyoxyethyl)methacrylate (EOEMA) and (hydroxyethyl)methacrylate (HEMA) copolymers as described in U.S. Pat. No. 6,517,750, available from Benz R&D (Sarasota, Fla.). One comprises a colorless IOL 25 material with no UV blocker (far left curve), one comprises the same colorless IOL 25 material with a UV blocker (middle curve), and the third is the same IOL 25 material but with pale yellow 3-hydroxykynurenine (far right curve). The graph illustrates that the 3-hydroxykynurenine has significant absorption in the blue region at about for example 400 nm to 450 nm.

Figure 5:
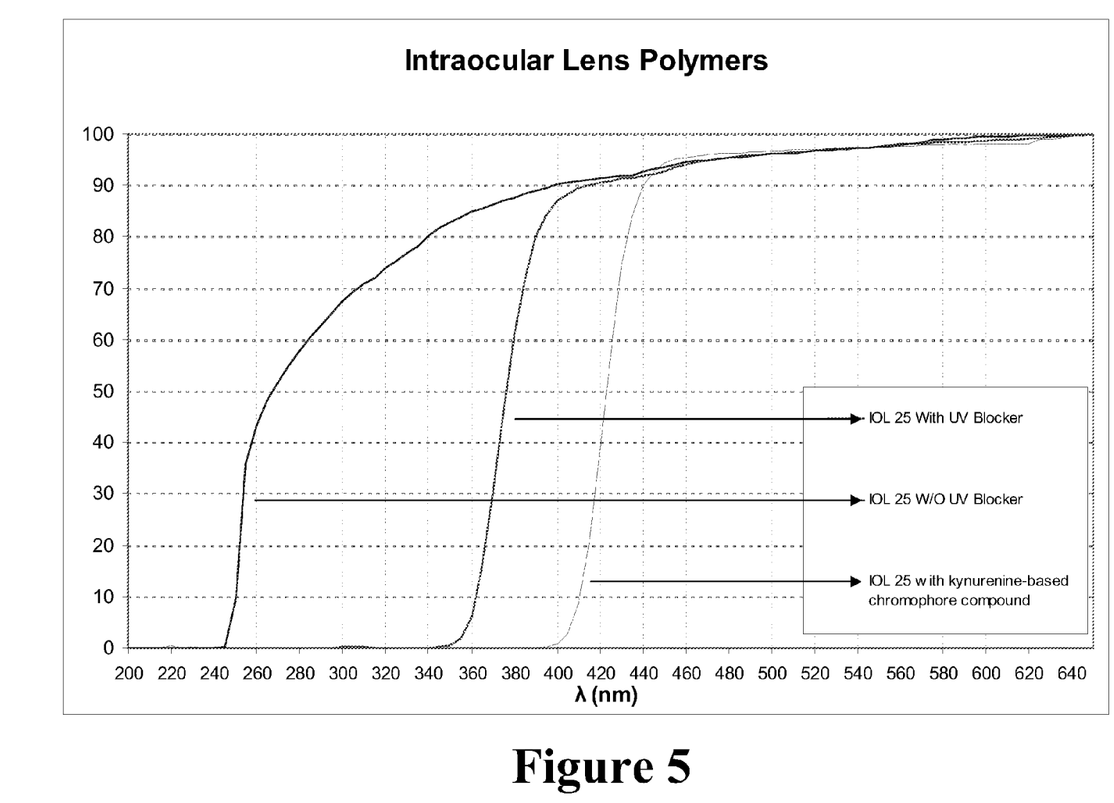
FIG. 5 illustrates transmission spectral properties, including one of a particular embodiment comprising a kynurenine-based compound.

FIG. 5 illustrates the UV-blocking and violet-blue filtering effect of the compound. Three transmission spectra are shown of a hydrophilic intraocular lens material including IOL 25 material of (ethyoxyethyl)methacrylate (EOEMA) and (hydroxyethyl)methacrylate (HEMA) copolymers as described in U.S. Pat. No. 6,517,750, available from Benz R&D (Sarasota, Fla.). One comprises a colorless IOL 25 material with no UV blocker (far left curve), one comprises the same colorless IOL 25 material with a UV blocker (middle curve), and the third is comprises the same IOL 25 material but with the kynurenine-based chromophore compound (far right curve).

Figure 6:
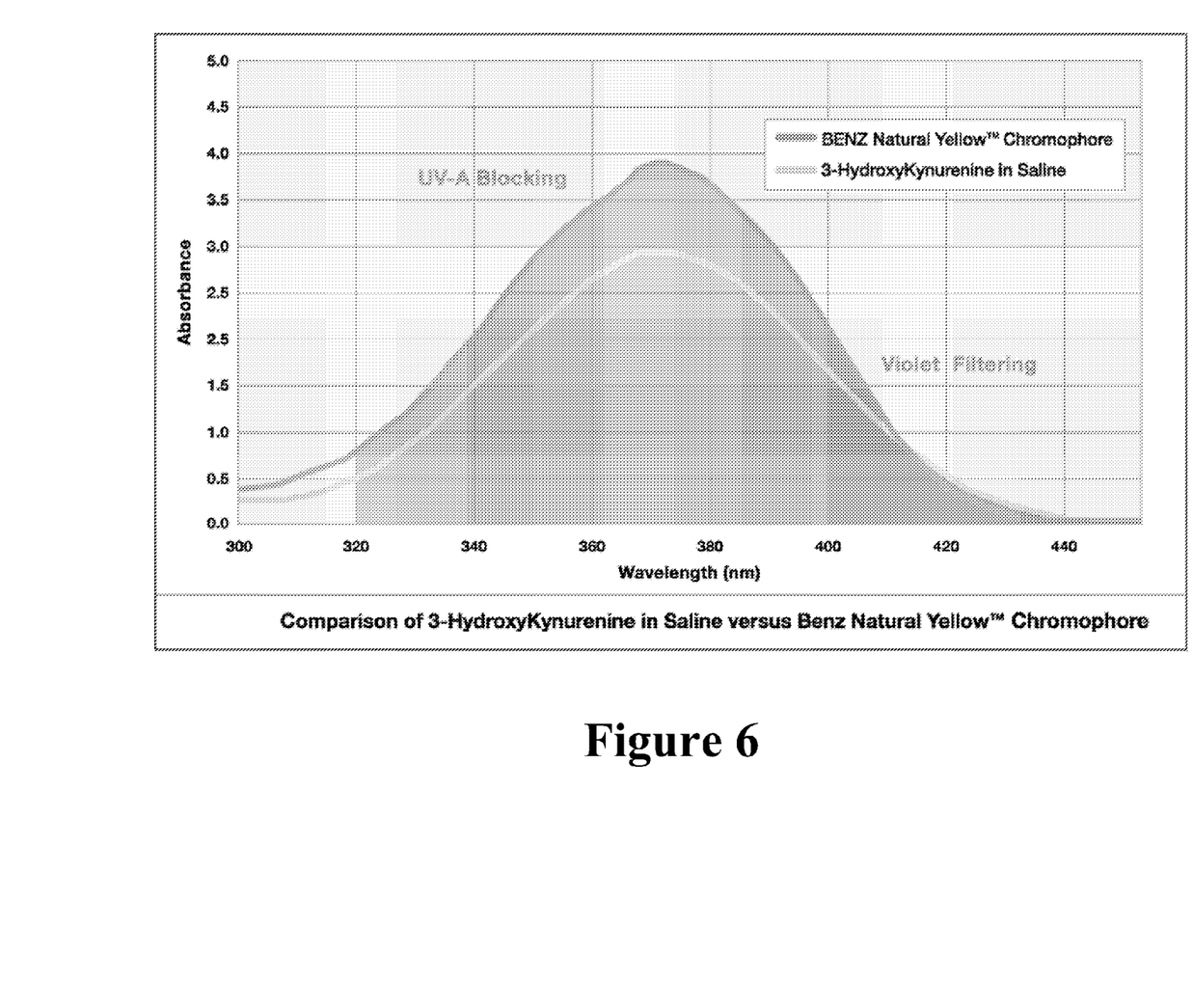
FIG. 6 illustrates transmission spectral properties between a particular embodiment and 3-hydroxykynurenine in saline.

FIG. 6 illustrates the performance of IOL 25 with the kynurenine-based chromophore compound (top profile) compared with 3-hydroxykynurenine in saline (bottom profile) in blocking UV-A and filtering violet light. Generally, 3-hydroxykynurenine chromophore has a broad absorption maximum at approximately 370 nm, which is near the middle of the UV-A range and a broad shoulder that extends out to 440 nm. The figure indicates that IOL 25 with the kynurenine-based chromophore compound is equivalent to 3-hydroxykynurenine in blocking UV-A and filtering violet light.

Figure 7:
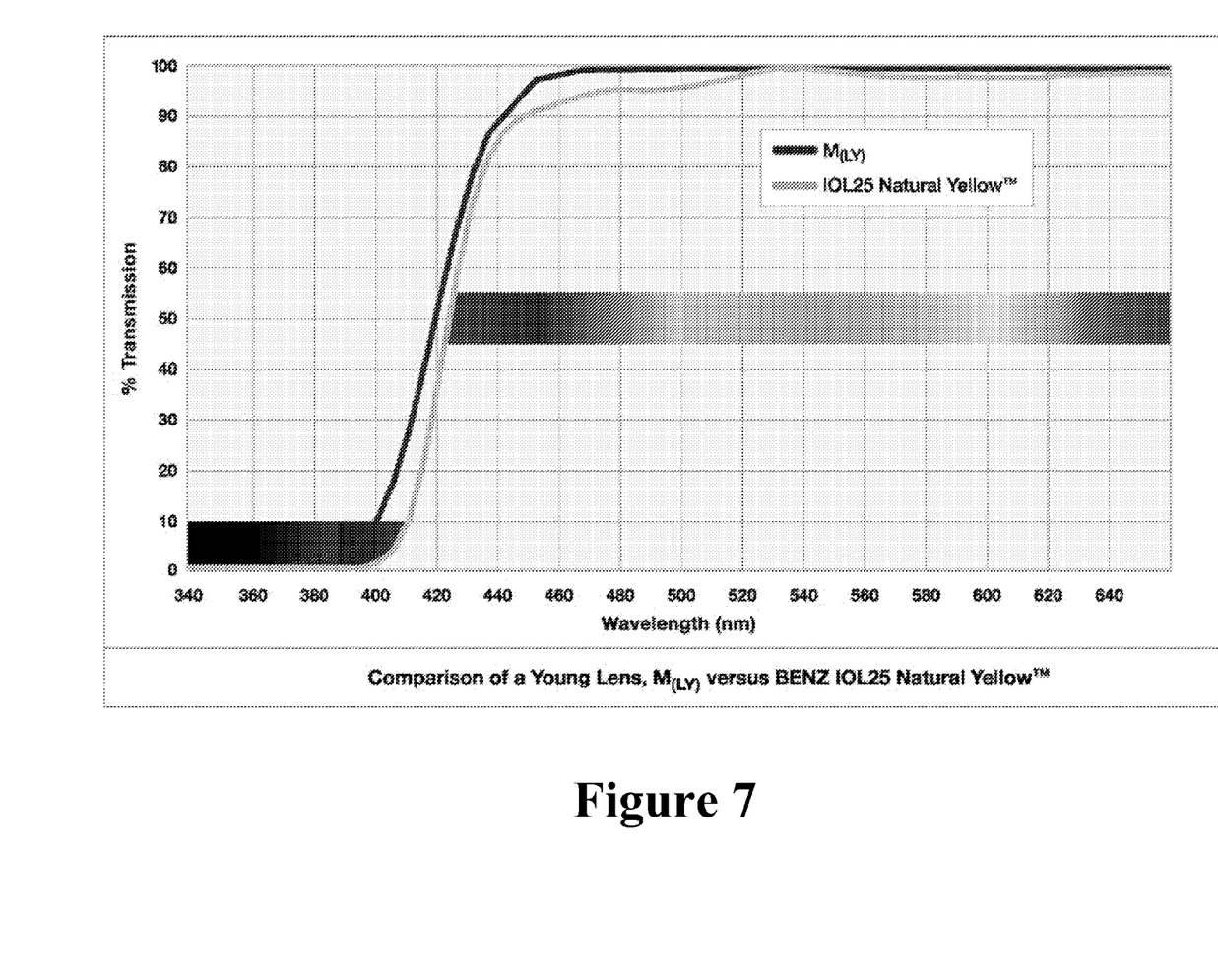
FIG. 7 illustrates transmission spectral properties between a particular embodiment and young human crystalline lens.

FIG. 7 illustrates the visible transmission spectrum of a 1.0 mm thick IOL 25 lens with the kynurenine-based chromophore compound (right curve) and of a young human crystalline lens (left curve). The IOL 25 material with 3-hydroxykynurenine is capable of protecting retina without blocking blue light.

Example 1

Preparation of 2-chloroethyl methacrylate

A solution of 530 ml (7.91 mol) of 2-chloroethanol and 1210 ml (14.96 mol) of pyridine in 3 L of EtOAc was cooled to 5° C. in an ice bath and a solution of 820 ml (6.71 mol) of methacryloyl chloride (tech., 80%) in 1 L of EtOAc was added so that the internal temperature was kept at less than or equal to 17° C. This took 2.5 hours. The reaction mixture was brought to room temperature slowly overnight. The slurry was then filtered and the cake of pyridine hydrochloride was washed with about 3 L of EtOAc. The filtrate was split into 3 approximately equal portions and each portion was thus worked up. Each was extracted with 2×1 L of 2N HCl, 2×500 ml of DI water and 1×500 ml of 5 wt % sodium bicarbonate and then the three were combined and dried over anhydrous sodium sulfate (764 g). After filtration, the EtOAc solution was treated with 11.1 g of hydroquinone and concentrated in vacuo to yield 1245.7 g of pale yellow oil. Vacuum distillation of this oil gave as the main cut 597.0 g (60%) of very pale yellow oil as product, by 82-89° C./>5 mm. GC analysis of the main cut showed the product to be 97.0% pure. The product was treated with 0.5 g of hydroquinone and stored in the freezer until used.

Example 2

Preparation of Kynurenine-Based Chromophore Compound

A reaction mixture containing 103.0 g (681 mmol) of 2-amino-3-hydroxyacetophenone, 125.1 g (842 mmol) of 2-chloroethyl methacrylate and 122.6 g (887 mmol) of potassium carbonate in 930 ml of DMSO was brought to 85° C. over 5 hours and stirred at that temperature overnight (16 hours). After this time, TLC (silica gel, hexane:acetone at 3:1) showed the reaction to be complete. After cooling to 48° C., the reaction mixture was partitioned between 2 L of DI water and 500 ml of toluene. After a second 500 ml toluene extraction of the aqueous phase, the combined organic layer was washed twice with 1 L of 10 wt % potassium carbonate. The organic phase was then passed through a plug of 1253 g of silica gel (70-230 mesh), eluting with hexane:acetone at 3:1 until no more product was visible (TLC) coming off the plug. This took 6 L of elution solvent. The eluant was concentrated in vacuo to yield 199 g of amber oil, which solidified while still hot.

The product was recrystallized from 5.5 L of hexane. At 64° C., a clear solution was obtained. After 4 hours cooling (T=35° C.) crystallization began. Stirring at room temperature overnight gave nice crystallization of the product. The slurry was filtered and washed with hexane (approximately 1 L) to give, after drying in vacuo to constant weight, 122 g (69.4%) of product as a yellow solid with mp 74-74.5° C. The material showed one spot by TLC and was 99.3% pure (HPLC).

What is claimed is:

1. A composition comprising: a compound comprising a polymerizable vinyl group covalently linked to a benzene ring-based chromophore comprising a ketone at the 1-position, a substituted or unsubstituted amino group at the 2-position, and an oxygen atom at the 3-position of the benzene ring, wherein the chromophore does not comprise an oxidative polymerization product of 3-hydroxykynurenine, and wherein the polymerizable vinyl group is linked to the chromophore through the oxygen atom at the 3-position of the benzene ring.

2. The composition according to claim 1, wherein the polymerizable vinyl group is linked to the chromophore via an alkylene or alkyleneoxy linker group.

3. The composition according to claim 1, wherein the polymerizable vinyl group comprises a methacrylate or acrylate moiety.

4. The composition according to claim 1, wherein the chromophore comprises at least one electron donating substituent in the 4-, 5-, or 6-position of the benzene ring.

5. The composition according to claim 1, wherein the carbonyl group at the 1-position of the chromophore is derivatized with an alkyl group.

6. The composition according to claim 1, wherein the oxygen atom at the 3-position of the chromophore is bonded to an aliphatic carbon atom.

7. The composition according to claim 1, wherein the compound is represented by

8. A composition comprising: a compound comprising a polymerizable vinyl group covalently linked to a benzene ring-based chromophore comprising a ketone at the 1-position, a substituted or unsubstituted amino group at the 2-position, and an oxygen atom at the 3-position of the benzene ring, wherein the chromophore does not comprise an oxidative polymerization product of 3-hydroxykynurenine, and wherein the polymerizable vinyl group is linked to the chromophore via a linker group, and wherein the polymerizable vinyl group is linked to the chromophore at the 3-position of the benzene ring.

9. A composition comprising: a compound comprising a polymerizable vinyl group covalently linked to a benzene ring-based chromophore comprising a ketone at the 1-position, a substituted or unsubstituted amino group at the 2-position, and an oxygen atom at the 3-position of the benzene ring, wherein the chromophore does not comprise an oxidative polymerization product of 3-hydroxykynurenine, and wherein the polymerizable vinyl group comprises a methacrylate or acrylate moiety which is linked to the chromophore via an alkylene or alkylenoxy linker group, and wherein the polymerizable vinyl group is linked to the chromophore at the 3-position of the benzene ring.

10. The composition according to claim 1, wherein the compound upon polymerization is suitable for use in ophthalmic lenses or devices.

11. The composition according to claim 1, wherein the compound upon polymerization is suitable for use as a UV blocker and visible light filter in ophthalmic lenses or devices.

12. A composition according to claim 1, wherein the chromophore comprises a substituent at the ketone of the 1-position of the benzene ring which does not comprise an amino acid group.

13. The composition according to claim 3, wherein the chromophore comprises at least one electron donating substituent in the 4-, 5-, or 6-position of the benzene ring.

14. The composition according to claim 3, wherein the carbonyl group at the 1-position of the chromophore is derivatized with an alkyl group.

15. The composition according to claim 3, wherein the oxygen atom at the 3-position of the chromophore is bonded to an aliphatic carbon atom.

16. The composition according to claim 8, wherein the chromophore comprises at least one electron donating substituent in the 4-, 5-, or 6-position of the benzene ring.

17. The composition according to claim 8, wherein the carbonyl group at the 1-position of the chromophore is derivatized with an alkyl group.

18. The composition according to claim 8, wherein the oxygen atom at the 3-position of the chromophore is bonded to an aliphatic carbon atom.

19. A composition comprising: a compound represented by wherein $R_1$ is H or alkyl, or comprises an amino acid moiety or derivative thereof;
wherein $R_2$ and $R_3$ are individually H or alkyl;
wherein $R_4$ comprises a polymerizable vinyl group; and
wherein X is an optional electron-donating group linked to the benzene ring at the 4, 5, or 6 position.

20. The composition according to claim 19, wherein the compound is represented by wherein R is H or alkyl, or comprises an amino acid moiety or derivative thereof;
wherein L is a linker; and
wherein PVG is a polymerizable vinyl group.

21. The composition according to claim 19, wherein the electron donating group is alkyl, alkoxy, or a substituted amino group.

* * * * *

UNITED STATES PATENT AND TRADEMARK OFFICE
CERTIFICATE OF CORRECTION

| | | |
|---|---|---|
| PATENT NO. | : 8,618,323 B2 | Page 1 of 1 |
| APPLICATION NO. | : 13/016829 | |
| DATED | : December 31, 2013 | |
| INVENTOR(S) | : Patrick H. Benz et al. | |

It is certified that error appears in the above-identified patent and that said Letters Patent is hereby corrected as shown below:

ON THE TITLE PAGE

Please correct the following paragraph:

(63) Please delete "Continuation-in-Part" and insert -- Divisional -- of -- U.S. -- Application Serial No. 12/042,317, filed on March 4, 2008, now U.S. Patent No. 8,026,326.

Signed and Sealed this
Fifth Day of August, 2014

Michelle K. Lee
*Deputy Director of the United States Patent and Trademark Office*